United States Patent [19]
Esser

[11] Patent Number: 5,222,977
[45] Date of Patent: Jun. 29, 1993

[54] SURGICAL NEEDLE WITH AN ADJUSTABLE EYE

[76] Inventor: René D. Esser, 881 Lurline Dr., Foster City, Calif. 94404

[21] Appl. No.: 839,650

[22] Filed: Feb. 21, 1992

[51] Int. Cl.5 .................................... A61B 17/32
[52] U.S. Cl. ................... 606/223; 606/144; 606/148; 606/222
[58] Field of Search ............... 606/222, 223, 224, 225, 606/226, 144, 148

[56] References Cited

U.S. PATENT DOCUMENTS

| | | | |
|---|---|---|---|
| 17,272 | 5/1857 | Garvey | 606/223 |
| 1,468,518 | 9/1923 | Scott | 606/148 X |
| 2,129,327 | 9/1938 | Kataja | 66/120 |
| 3,233,800 | 2/1966 | Catania | 606/225 X |
| 3,871,379 | 3/1975 | Clarke . | |
| 4,592,347 | 6/1986 | Mahruki | 606/206 |
| 4,641,652 | 1/1987 | Hutterer et al. . | |
| 4,760,848 | 8/1988 | Hasson . | |
| 4,923,461 | 5/1990 | Caspari et al. . | |

FOREIGN PATENT DOCUMENTS 2532242  2/1977  Fed. Rep. of Germany ...... 606/223

OTHER PUBLICATIONS

Hanks et al., *Orthopaedic Review*, vol. XIX, No. 6, Jun. 1990, pp. 541-548.
Barber et al., *J. Bone and Joint Surgery*, vol. 67-B, No. 1, Jan. 1985, pp. 39-41.
Wirth, *Clinical Orthopaedics and Related Research*, No. 157, 1981, pp. 153-160.
Gillquist et al., *Clinical Orthopaedics and Related Research*, No. 167, 1982, pp. 29-33.
DeHaven, *J. Bone and Joint Surgery*, vol. 63-B, No. 3, 1981. p. 463.
C. E. Henning et al., *J. Arthroscopic and Related Surgery*, vol. 3, No. 1, 1987, pp. 13-18.

Primary Examiner—Stephen C. Pellegrino
Assistant Examiner—Jeffrey A. Schmidt
Attorney, Agent, or Firm—Townsend and Townsend Khourie and Crew

[57] ABSTRACT

A surgical needle comprising an elongate shaft having proximal and distal ends, said distal end further comprising an eye which can be opened and closed, and said elongate shaft further comprising a means for opening and closing said eye. The needle may be securely affixed to a handle for convenient use. The needle may be used to place sutures in a wide variety of applications.

22 Claims, 4 Drawing Sheets

SURGICAL NEEDLE WITH AN ADJUSTABLE EYE

BACKGROUND OF THE INVENTION

1. Field of the Invention

The present invention relates generally to medical instruments and, more specifically, to apparatus and methods for suturing tissue. The apparatus and methods are particularly useful for the repair of tissue lacerations in closed spaces such as meniscal lacerations in the knee, and the like.

A variety of injuries and diseases, including many which previously required surgery, may be diagnosed and treated through scope-type medical instruments. Fiber optic arthroscopes are representative of these devices. Using an arthroscope, a physician may confirm the presence of lesions detected by other diagnostic methods as well as reveal lesions that have been missed. A physician may also repair some lesions through an arthroscope.

Since arthroscopes are introduced through relatively small surgical incisions, arthroscopic procedures are less invasive than open surgical procedures. Because arthroscopic procedures are less invasive, they are less costly and are associated with less morbidity than open procedures. Arthroscopic procedures are often done on an outpatient basis.

In addition to the diagnostic value of arthroscopic procedures, a variety of therapeutic procedures may be performed through an arthroscope. For example, meniscectomy (surgical removal of a meniscus in the knee) may be performed through an arthroscope.

Although meniscectomy is performed on meniscal injuries, meniscal repair is advisable for many meniscal injuries, e.g., vascular zone lacerations. Hanks et al., *Orthopaedic Review*, 19(6):541-548 (1990). Meniscal repair requires approximation and fixation of the edges of the meniscal laceration with sutures. When repaired arthroscopically, suturing the meniscal laceration must be done in a small closed space.

Several techniques have been developed to place sutures in the meniscus during arthroscopic repair. In one technique, a double cannula is placed within the knee joint. Two 10 inch needles with suture attached are directed to the meniscal body at the site of the laceration through the double cannula. The needles are pushed through the meniscus and retrieved in an incision on the opposite side of the meniscus. The suture is knotted at the point where the needles exit the joint.

In an alternative method of arthroscopically suturing meniscal tears, a large bore needle is passed from an incision outside the knee joint through the meniscal tear and body. The suture is placed through the needle into the joint. The end of the suture is brought out of the joint with an arthroscope and knotted. The needle is withdrawn, the suture pulled back into the joint and abutted into the meniscal body. Another suture is similarly placed in close proximity to the first. The two sutures are tied in the incision through which the needle passed.

Even with the availability of the above instruments, tissue repair and suture placement are difficult and time consuming for many physicians. Thus it is desirable to provide improved apparatus and methods for placing sutures in a remote and confined space. The apparatus should be able to reach the target location while requiring minimal work space. Furthermore, the techniques using the apparatus to place sutures should not be cumbersome to perform and should rely on dexterity skills which a surgeon already possesses. The present invention fulfills this and other needs.

2. Description of the Background Art

Many devices in general medical use are employed for suturing in closed spaces. For example, large bore spinal needles have been used as a conduit to transport sutures through meniscal bodies and joint capsules. Hanks et al., supra. Keith needles are also used to place sutures arthroscopically. Barber et al., *J. Bone and Joint Surgery*, 67-B(1):39-41 (1985). Keith needles are straight needles which are manufactured either with suture attached to the proximal end of the needle or with a permanently closed eye for threading suture.

Other devices have been developed specifically for closed space suture placement through a scope. The Henning needle-holder is specifically adapted for arthroscopically placing sutures. The Henning needle-holder firmly holds needles in such a way as to allow a surgeon to precisely control suture placement.

U.S. Pat. No. 3,871,379 describes instruments for laproscopic suturing. The suture needle is secured to a needle-holder capable of altering the alignment between the needle and needle-holder. The needle has an open protuberance at the distal end to hold the suture.

U.S. Pat. No. 4,641,652 describes a device to endoscopically tie knots in suture. The device does not assist suture placement.

U.S. Pat. No. 4,760,848 describes a rotational surgical instrument which may be used for endoscopically placing sutures. The instrument includes a rotating head comprising a pair of jaws. The jaws may be closed to hold a needle. Rotation of the head allows curved needles to penetrate tissue and place suture.

U.S. Pat. No. 4,923,461 describes a suturing instrument useful in arthroscopic surgery. The instrument, which resembles a conventional grasper and forceps-type microsurgical instrument, includes a hollow tip for engaging tissue to be sutured and a recess for securing a hollow tubular needle through which to pass suture.

The disclosures of each of the foregoing references are incorporated herein by reference.

SUMMARY OF THE INVENTION

The present invention comprises novel apparatus and methods for placing sutures. One element common to all aspects of the present invention is a surgical needle-like device having an eye which may be opened and closed. One apparatus of the present invention comprises an elongate shaft having proximal and distal ends, the distal end further comprising an eye which can be opened and closed, and the shaft further comprising a means for opening and closing the eye. A handle may be securely affixed to the proximal end of the elongate shaft for convenient use.

The means for opening and closing the eye may have a variety of configurations, but should be sufficiently accessible to allow easy manipulation during use by a surgeon. In an exemplary embodiment, the means for opening and closing the eye comprises a blade which is at least partially contained within a longitudinal gutter in the shaft. The blade position determines whether the eye is open or closed. The blade position is controlled by a knob located proximally on the shaft.

The apparatus of the present invention may be used in a variety of surgical procedures. One procedure is arthroscopic repair of meniscal lacerations. The apparatus of the present invention may be directed from either within or outside the knee joint to repair meniscal lacerations. Other surgical procedures in which the apparatus of the present invention may be useful will be readily appreciated by those of skill in the art.

DESCRIPTION OF THE PREFERRED EMBODIMENTS

According to the present invention, novel apparatus and methods are provided for placing sutures. The apparatus and methods are particularly useful in placing sutures in a closed space. One element common to all aspects of the present invention is a surgical needle-like device having an eye which can be opened and closed. The ability to open and close the eye of the surgical needle-like device allows surgeons to practice improved methods of suture placement.

One apparatus of the present invention comprises an elongate shaft having proximal and distal ends, the distal end further comprising an eye which can be opened and closed, and the shaft further comprising a means for opening and closing the eye. A handle may be securely affixed to the proximal end of the elongate shaft for convenient use.

The means for opening and closing the eye may have a variety of configurations, but should be sufficiently accessible to allow easy manipulation during use by a surgeon. In an exemplary embodiment, the means for opening and closing the eye comprises a blade which is at least partially contained within a longitudinal gutter in the shaft. The blade position determines whether the eye is open or closed. The blade position is controlled by a knob located near the junction of the shaft and the handle.

One element of the present invention is an elongate shaft having proximal and distal ends. Generally, the shaft will have a needle-like point at the distal end. The pointed shape of the distal shaft will facilitate penetration of tissues and lessen trauma to the penetrated tissue.

The cross sectional shape of the elongate shaft will generally be circular, although this is not critical. The cross sectional shape of the elongate shaft may vary through the length of the shaft. In a preferred embodiment, the elongate shaft has an ovoid cross section at the eye with the longest dimension perpendicular to the axis of the eye. The largest dimension of the cross sectional area of the elongate shaft will generally be in the range of 0.5 mm to 1.5 mm, usually 0.75 mm to 1.25 mm, and preferably about 1.0 mm. The length of the elongate shaft may generally be in the range of 80 mm to 250 mm, usually 100 mm to 150 mm, and preferably about 130 mm. Longer or shorter elongate shafts may be fashioned for specialized uses.

The elongate shaft will be constructed of a rigid material such as stainless steel or the like. The elongate shaft may be straight or curved. When curved, the curvature will generally be located distally on the elongate shaft. The angle of curvature is not critical and may vary. Generally, the angle of curvature will be in the range of 15° to 45°, usually in the range of 25° to 35°, and preferably about 30°.

Another element of the present invention is an eye in the elongate shaft. One unique aspect of the eye is that it may be opened and closed. Hereinafter, the term "closed" indicates that the entire circumference of the eye is demarcated by a solid structure. Also, hereinafter, the term "open" indicates that at least a portion of the circumference of the eye is not demarcated by a solid structure.

The distance between the eye and the distal end of the elongate shaft is not critical and may vary. Generally, the eye will be disposed distally on the elongate shaft in the range of 4 mm to 10 mm from the distal end, usually 5 mm to 8 mm from the distal end, and preferably about 6 mm from the distal end.

When closed, the shape of the eye is not critical and may vary. Preferably, the cross section of the eye in the closed position will be generally semi-circular. Likewise, the shape of the eye in the open position is not critical and may vary. Preferably, when open, the eye will have at least one solid protuberance projecting into the open region of the eye's circumference. The protuberance will generally form a hook-like projection into the open region of the eye's circumference. The protuberance may be used to facilitate insertion of the suture into the eye. The radius of the eye in the closed position must be sufficient to allow suture material to be inserted and removed from the eye when in the open position. Generally, the radius of the eye is about one-half the radius of the elongate shaft at the site of the eye. The radius of the eye may vary to accommodate sutures of different radii.

The cross sectional area of the elongate shaft may vary along its length. In the case of elongate shafts having a circular cross section, an increased cross sectional area corresponds to an increase in the diameter of the circular cross section. Preferably, the cross sectional area will be increased in the portion of the shaft surrounding the eye. The cross sectional area may be increased by as much as 100%. The length of the shaft having an increased cross sectional area may be as much as 15 mm. In embodiments in which the cross sectional area of the shaft varies, the cross sectional area changes gradually so as to minimize tissue trauma caused by passing the region of increased cross sectional area through tissue.

Another element of the invention is a means for opening and closing the eye. Typically, the eye will be opened and closed by means of a blade. The blade extends along the elongate shaft proximally from the eye. The distal portion of the blade demarcates a portion of the circumference of the eye when the eye is in the closed position. The blade may also demarcate a portion of the circumference of the eye when the eye is in the open position. The blade may be rigid or semi-rigid and comprised of stainless steel or the like. Preferably, the blade may be removed from the elongate shaft. Removal of the blade facilitates cleaning and sterilization of the instrument.

In a preferred embodiment, a protuberance extends laterally and distally from the lateral aspect of the distal end of the blade. When the blade is extended the protuberance forms a portion of the circumference of the eye. The protuberance is smooth and formed so as to correspond to the surface of the elongate shaft distal to the eye when the eye is closed. The smooth surface of the protuberance gives the elongate shaft an unbroken profile when the eye is closed. The smooth unbroken profile allows passage of the elongate shaft through tissue with minimum trauma.

The blade is movable along the elongate shaft. When the eye is closed, the blade is in the extended position. When the eye is open, the blade is in the withdrawn position. The position of the blade may be controlled by a positioning means. The positioning means must be located so that it is accessible to a surgeon during use. The positioning means is generally located near the proximal end of the elongate shaft, however, this is not critical and may vary. In a preferred embodiment, the positioning means is a knob securely affixed to the blade. The knob protrudes perpendicularly from the proximal end of the shaft. The knob has freedom of movement along the axis of the elongate shaft. Movement of the knob results in movement of the blade along the elongate shaft. Pushing the knob toward the distal end of the shaft will advance the blade distally so as to close the eye. Pulling the knob proximally will withdraw the blade so as to open the eye. Alternatively, a notch, the blade itself, or other similar mechanical means may be employed to position the blade.

Preferably, the blade will be at least partially contained within a gutter that extends proximally from the eye to the positioning means. The shape of the gutter is not critical and may vary. Typically, the gutter has a cross sectional shape which is approximately rectangular. The depth of the gutter is determined by the width of the blade. At least 50% of the width of the blade must fit within the gutter. Preferably, the entire blade will fit within the gutter through at least a portion of the blade's length. When present, the above described protuberance lies external to the gutter. A lubricous material may be applied to the walls of inner surface of the gutter to facilitate sliding the blade. Alternatively, a lubricous sleeve or coating may be disposed over a portion of the blade within the gutter to facilitate sliding. The lubricous material, sleeve, or coating is conveniently formed from a highly lubricous plastic such as nylon, polytetrafluoroethylenes (e.g., Teflon®), and the like. A similar lubricous plastic may be employed to facilitate sliding of the positioning means.

Distally, the gutter originates at the eye. The gutter may extend to the proximal end of the elongate shaft or terminate distal to the proximal end of the elongate shaft. In a preferred embodiment the superior aspect of the proximal end of the elongate shaft is flat and depressed. The gutter terminates at the distal end of the depression. Two posts extend superiorly from the proximal region of the depression. The blade is joined to a rectangular block which slides on the flat surface of the depression. The rectangular block has a protrusion from the proximal end formed so as to lie between the posts on the depression. The posts provide lateral support to the rectangular block and guide the movement of the block. The blade is affixed to the lateral aspect of the distal end of the rectangular block. The blade may be removed from the elongate shaft by lifting the protrusion from the proximal end of the rectangular block from between the posts and sliding the blade proximally out of the gutter. The blade may be inserted by sliding the blade distally into the gutter and fitting the rectangular block between the posts. The posts act to hold the blade in the gutter when in use by limiting the distal movement of the blade. A knob is located on the superior aspect of the rectangular block to control movement of the blade.

A handle may be securely affixed to the proximal end of the elongate shaft. The handle is rigid to allow precise manipulation of the elongate shaft. The shape of the handle is not critical and may vary. The size of the handle may likewise vary. Generally the length of the handle will be in the range of 80 mm to 150 mm, usually 110 mm to 130 mm and preferably about 120 mm. The width of the handle will generally be in the range of 10 mm to 15 mm and may vary along the length of the handle. The height of the handle will generally be in the range of 5 mm to 11 mm, usually 6 mm to 9 mm and preferably about 7 mm. The handle may comprise a variety of rigid materials such as stainless steel and the like.

The apparatus of the present invention has a wide variety of uses. Although the apparatus is particularly useful for placing sutures in closed spaces, it may also be used to place sutures in open locations. The apparatus described above allows the practice of a novel method of suture placement. The method may be practiced to place sutures in any type of surgical procedure, such as laceration repair, surgical incision closure, approximation of intact tissues, fixation of foreign objects, and the like. Below, the general method is described in the context of laceration repair. A person of skill in the art will readily appreciate the general utility of the method.

As used hereinafter, the phrase "end of a suture" will be understood to indicate a region generally disposed toward one terminus of suture material. It will be understood by a person of skill that the portion of the suture located within the eye will vary according to the use. The placement of suture in the eye must provide sufficient suture material beyond the eye for securing the suture by whatever means chosen by the surgeon.

A meniscal laceration may be repaired by using the apparatus of the present invention from either within or outside the knee joint. As used herein, the knee joint is the interior space created by the knee joint capsule. Repair from within the knee joint indicates that the suturing device is begins and ends the placement of the sutures from within the knee joint. Repair from outside the knee joint indicates that the suturing device begins and ends the placement of the sutures outside the knee joint. When the repair is done arthroscopically, an arthroscope is used to visualize the procedure and aid in manipulation of instruments and suture within the knee joint. In arthroscopic repairs within the knee joint, the apparatus of the present invention may be introduced into the knee joint under control of an arthroscope or through an arthroscope.

Generally, to repair a meniscal laceration from within a knee joint using the present invention in which the elongate shaft forms a needle, the needle is passed through a selected location of the meniscus and the laceration so that the eye of the needle is exterior to the knee joint. The eye is closed when being passed through tissue. When the eye is outside the knee joint and accessible to the surgeon, the eye is opened, a first end of a suture in placed in the eye, and the eye is closed. The needle is then withdrawn from the meniscus so that the eye is in the knee joint and the first end of a suture traverses the meniscus. A second end of a suture remains exterior to the knee joint.

The needle, still holding the first end of a suture in the eye, is passed through the meniscus and laceration in a location other than the selected location so that the eye is exterior to the knee joint. The eye is opened, the first end of a suture is removed from the eye, and the eye is closed. The needle is then completely withdrawn from the meniscus. The first end of a suture remains in place outside the knee joint. The first and second ends of the suture are secured as by surgical knots. Generally, the first and second ends of a suture are opposite ends of the same suture although this is not critical. These steps are repeated until the until the laceration is repaired. Complete repair is determined by the surgeon. The nature of the laceration will dictate how many sutures are needed, the location of the sutures in the meniscus and the laceration, and how best to secure the suture ends.

Generally, to repair a meniscal laceration from outside a knee joint using the present invention in which the elongate shaft forms a needle, a first end of a suture is placed in the eye and the eye is closed. The needle is outside the knee at this step. The needle is passed through a selected location of the meniscus and the laceration so that the eye is within the knee joint and a second end of a suture remains outside the knee joint. The eye is opened and the first end of a suture is removed from the eye. The eye is then closed and the needle withdrawn from the knee joint. The first end of a suture remains inside the knee joint.

The needle is then passed through a location of the meniscus and the laceration other than the selected location so that the eye is within knee joint. The eye of the needle is opened, the first end of a suture is placed in the eye, and the eye is closed. An eye having a hook-like shape when open facilitates placing suture in the eye within the knee joint. The suture and the needle can be manipulated to allow the eye to hook the suture. The eye can then be closed to hold the suture. The needle is completely withdrawn from within knee joint bringing the first end of a suture outside the knee joint. The eye is opened and the first end of a suture is removed from the eye. The first and second ends of a suture are secured. The above steps are repeated until the laceration is repaired. Complete repair is determined by the surgeon. The nature of the laceration will dictate how many sutures are needed, the location of the sutures in the meniscus and the laceration, and how best to secure the suture ends.

Figure 1:
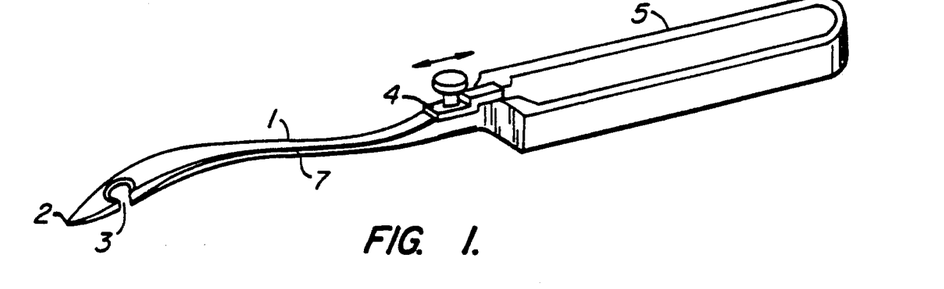
FIG. 1 illustrates a perspective view of a surgical needle with an adjustable eye constructed in accordance with the principles of the present invention.

Referring now to the figures, FIG. 1 illustrates a perspective view of a specific embodiment of the invention. The elongate shaft 1 has a distal end 2 which is pointed. The eye 3 is disposed distally on the elongate shaft 1. The eye 3 is in the open position. Proximally, the elongate shaft 1 is attached to the handle 5. The positioning means 4 is located at the proximal end of the elongate shaft 1 near the junction with the handle 5. The blade 7 extends proximally from the eye to the positioning means 4. In the illustration, the cross-sectional dimension of the elongate shaft 1 is increased in the area surrounding the eye 3. The elongate shaft 1 is also curved.

Figure 2A:
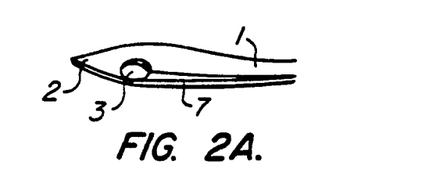
FIGS. 2A-C illustrate three embodiments of the distal tip of a surgical needle with an adjustable eye constructed in accordance with the principles of the present invention.
Figure 2B:
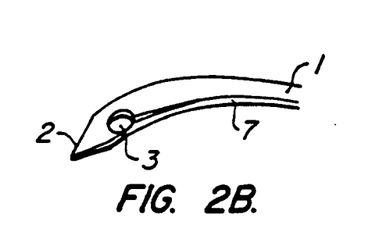
Figure 2C:
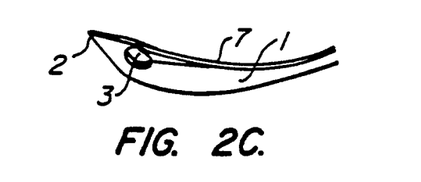

FIGS. 2A–B illustrate two embodiments of the distal end of the elongate shaft 1. FIG. 2A demonstrates a straight elongate shaft 1. FIGS. 2B and 2C illustrate an elongate shaft 1 curved in its distal portion. Although the curvature is located proximal to the eye 3 in the illustration, the curvature may also be distal to the eye 3 for specialized applications. The curvature may be horizontal, vertical, or both in respect to the handle.

Figure 3A:
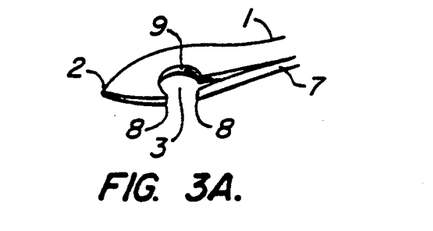
FIGS. 3A-B illustrate the eye of one embodiment of the present invention in both the open and closed positions.
Figure 3B:
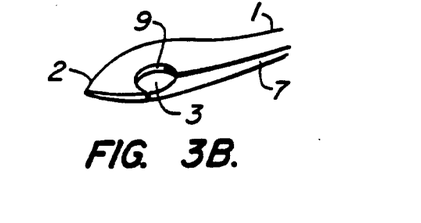

FIGS. 3A–B illustrate the eye 3 in the elongate shaft 1 in the open and closed positions. FIG. 3A demonstrates the eye 3 in the open position. The blade 7 is withdrawn. In this embodiment, two protuberances 8 are formed in the opening of the eye 3 in the elongate shaft 1. The protuberances 8 have a hook-like shape which facilitates placing suture in the eye 3. The solid boundary of the eye 9 is illustrated in the open position. The solid boundary of the eye 9 does not completely enclose the eye 3 when the eye 3 is in the open position.

FIG. 3B illustrates the eye 3 in the elongated shaft 1 in the closed position. The blade 7 is in the extended position. In the closed position, the blade 7 demarcates a portion of the solid boundary 9 of the eye 3. The solid boundary 9 of the eye 3 is illustrated in the closed position. The solid boundary of the eye 9 completely encloses the eye 3 when the eye 3 is in the closed position.

Figure 4A:
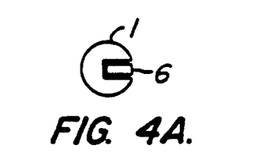
FIGS. 4A-C illustrate three views of a gutter in the shaft of one embodiment of the present invention.
Figure 4B:
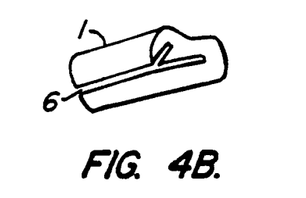
Figure 4C:
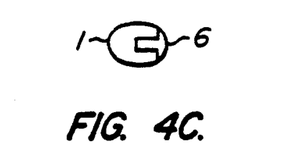

FIGS. 4A–C illustrate different views of a gutter 6 in a elongate shaft 1 in a surgical needle with an adjustable eye in one embodiment of the present invention. FIG. 4A illustrates a cross sectional view of the proximal portion of an elongate shaft 1. FIG. 4C illustrates the cross section of the distal portion of an elongate shaft 1. The gutter 6 extends from about the center of the elongate shaft 1 to the perimeter. In this particular embodiment, the gutter 6 is approximately rectangular, although the shape is not critical and may vary.

FIG. 4B illustrates a gutter 6 at the junction of an elongate shaft 1 and handle 5. When in position, the blade protrudes from the proximal end of the gutter 6 to join the means for opening and closing the eye.

Figure 5A:
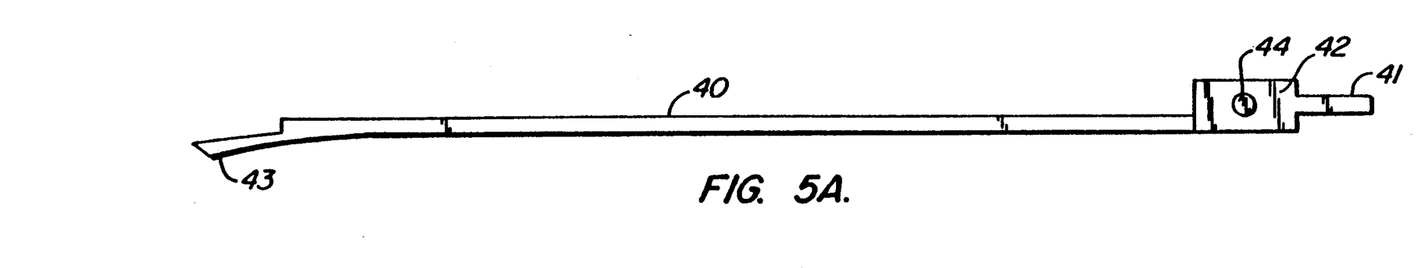
FIGS. 5A-C illustrate three views of a blade constructed in accordance with the principles of the present invention.
Figure 5B:
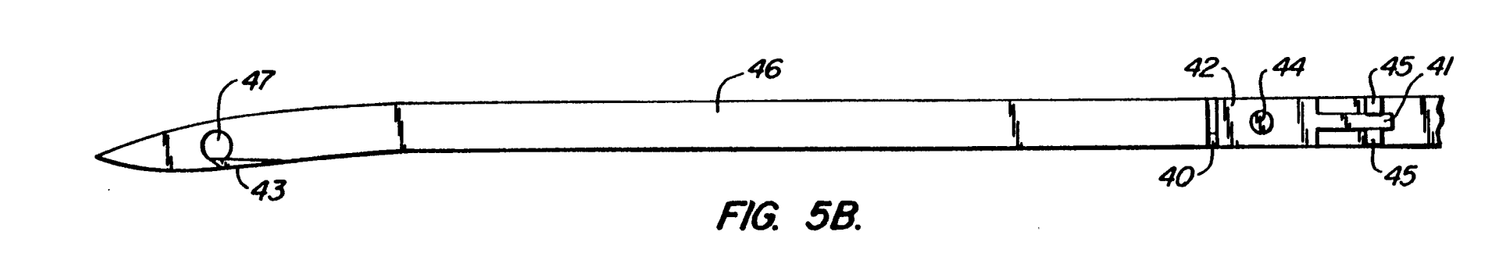
Figure 5C:
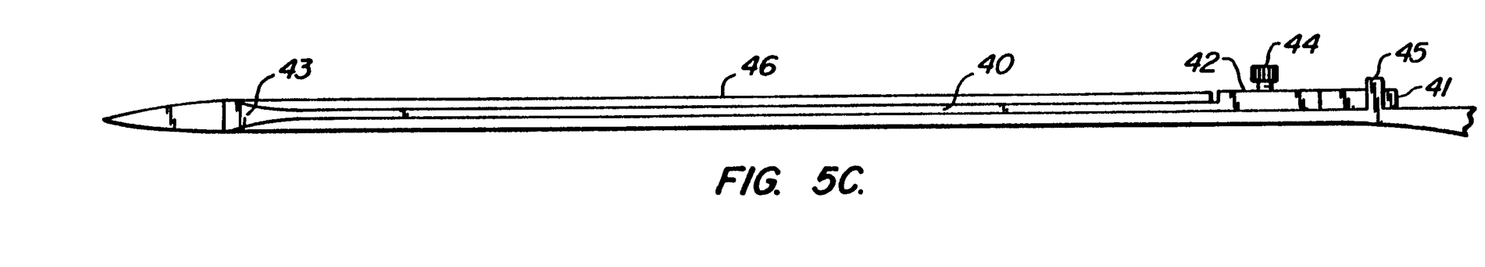

FIGS. 5A–C illustrate one embodiment of a blade. FIG. 5A demonstrates the superior view of a blade 40. Distally the blade 40 is joined to a protuberance 43. The protuberance 43 is formed so as to close the eye when the blade 40 is in the extended position. Proximally, the blade 40 is affixed to the lateral aspect of the distal end of a rectangular block 42. A knob 44 to control movement of the blade 40 is located on the superior surface of the rectangular block 42. A protrusion 41 is located on the proximal end of the rectangular block 42.

FIG. 5B illustrates a superior view of one embodiment of an elongate shaft with a blade in place. The blade 40 is in the extended position and the eye 47 is closed. The protuberance 43 forms a portion of the circumference of the eye 47. The blade 40 is affixed to the lateral aspect of the distal end of a rectangular block 42. A knob 44 is located on the superior aspect of the rectangular block 42. A protrusion 41 extends distally from the distal end of the rectangular block 42. The protrusion 41 lies between posts 45 located on the elongate shaft 46. The blade 40 lies out of view in a gutter in the elongate shaft 46.

FIG. 5C illustrates a lateral view of one embodiment of an elongate shaft with a blade in place. The protuberance 43 is joined to the blade 40. The blade 40 lies in a gutter in the elongate shaft 46. Proximally, the blade is joined to a rectangular block 42. A knob 44 is located on the superior surface of the rectangular block 42. The rectangular block 42 lies in a depression in the superior surface of the elongate shaft 46. A protrusion 41 extends from the distal end of the rectangular block 42. The protrusion 41 lies between posts 45 extending superiorly from the depression in the elongate shaft 46.

Figure 6A:
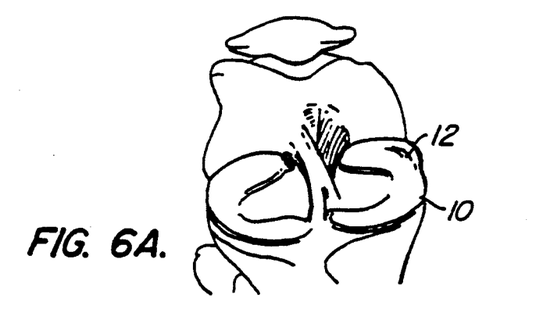
FIGS. 6A-F illustrate repair of a meniscal laceration from inside the knee joint in accordance with the principles of the present invention.

FIGS. 6A–F illustrate suture placement through a laceration 12 in the medial meniscus 10 from within the knee. FIG. 6A illustrates the anatomy of a laceration 12 in the posterior aspect of the medial meniscus 10.

Figure 6B:
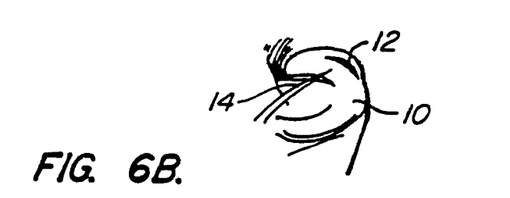

Referring to FIG. 6B, the surgeon identifies the desired placement location of the first end of the suture 16 in the medial meniscus 10 and passes the distal end of the elongate shaft 14 through tissue of the medial meniscus 10 on one side of the laceration 12. The distal end of the elongate shaft 14 is then passed through tissue of the medial meniscus 10 on the opposite side of the laceration 12. The elongate shaft 14 is advanced until the eye 20 of the elongate shaft 14 is accessible to the surgeon outside the knee joint. While passing through tissue, the eye 20 in the elongate shaft 14 is preferably in the closed position. If the eye 20 in the elongate shaft 14 is in the open position while passing through tissue, the eye 20 may catch and tear tissue similar to a Cope ® biopsy needle.

Figure 6C:
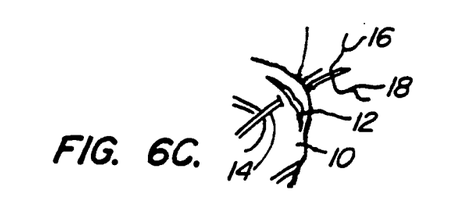
Figure 6D:
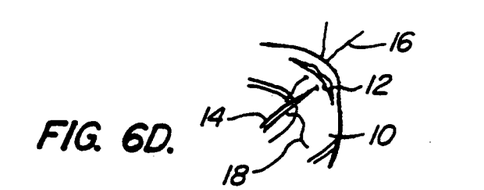

As shown in FIG. 6C, when the elongate shaft has passed through the tissue on both sides of the laceration 12 and the eye 20 is accessible to the surgeon, the eye 20 is opened. A first end of a suture 16 is placed in the open eye 20. The eye 20 is then closed.

The elongate shaft 14 is withdrawn from the tissue of the meniscus 10 pulling the first end of a suture 16 through the tissue of the meniscus 10. The first end of a suture 16 remains in tissue on both sides of the laceration 12 of the meniscus 10 (see FIG. 6D).

Figure 6E:
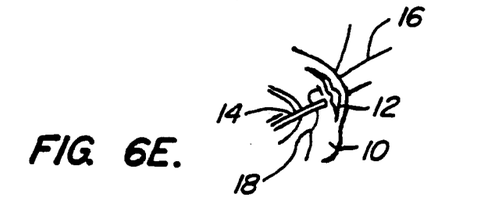
Figure 6F:
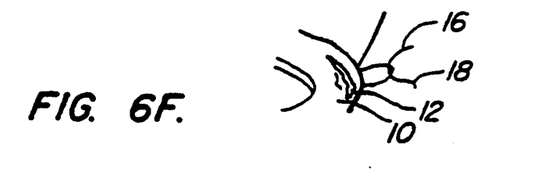

As illustrated by FIG. 6E, the surgeon then passes the elongate shaft 14 through tissue on both sides of the laceration 12 of the meniscus 10. The first end of a suture 16 remains in the closed eye 20 of the elongate shaft 1. A second end of a suture 18 is left outside the knee joint. The elongate shaft 14 is advanced until the eye 20 in the elongate shaft 14 is accessible to the surgeon. The eye 20 is opened and the first end of a suture 16 is removed. The elongate shaft 14 is withdrawn from the tissue of the meniscus 10. The first end of the suture 16 remains outside of the knee joint. The first end of a suture 16 and the second end of a suture 18 are secured thereby approximating the two sides of the laceration 12 (FIG. 6F).

Figure 7A:
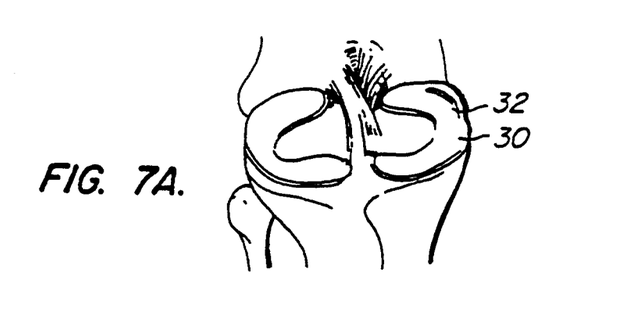
FIGS. 7A-F illustrate repair of a meniscal laceration from outside the knee joint in accordance with the principles of the present invention.

Repair of a laceration in a meniscus may also be accomplished by directing the apparatus of the present invention from outside the knee joint. FIG. 7A illustrates the anatomy of a laceration 32 in the posterior aspect of the medial meniscus 30.

Figure 7B:
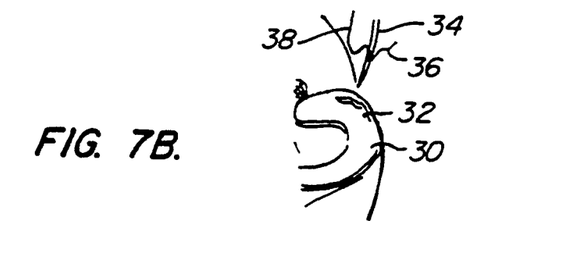

Outside the knee joint, the surgeon places one end of a suture 36 in the open eye 40 in the elongate shaft 34. The eye 40 is then closed (see FIG. 7B). The distal end of the elongate shaft 34 is then passed through tissue of the meniscus 30 on the opposite sides of the laceration 32. The elongate shaft 34 is advanced until the eye 40 of the elongate shaft 34 is inside the knee joint. While passing through tissue, the eye 40 in the elongate shaft 34 is preferably in the closed position.

Figure 7C:
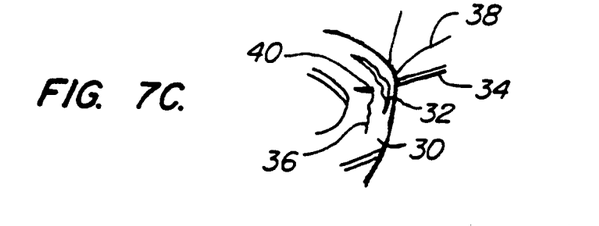

As shown in FIG. 7C, when the elongate shaft has passed through the tissue on both sides of the laceration 32 and the eye 40 is within the knee joint, the eye 40 is opened. The first end of a suture 36 is removed from the open eye 40. The eye 40 is then closed.

Figure 7D:
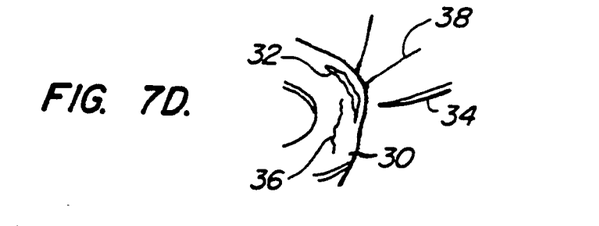

The elongate shaft 34 is withdrawn from the tissue of the meniscus 30. The first end of a suture 36 remains in tissue on both sides of the laceration 32 of the meniscus 30 (see FIG. 7D). A second end of a suture 38 remains outside the knee joint.

Figure 7E:
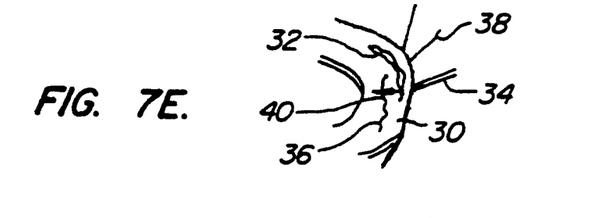
Figure 7F:
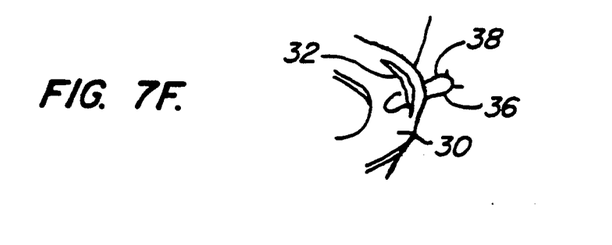

As illustrated by FIG. 7E, the surgeon then passes the elongate shaft 34 through tissue on both sides of the laceration 32 of the meniscus 30 until the eye 40 is in the knee joint. The eye 40 in the elongate shaft 34 is opened and the first end of a suture 36 is placed in the open eye 40. The eye 40 is closed, holding the first end of a suture 36. The elongate shaft 34 is withdrawn from the knee joint. The eye 40 is opened and the first end of a suture 36 is removed. The first end of the suture 36 is outside of the knee joint. The first end of a suture 36 and the second end of a suture 38 are secured thereby approximating the two sides of the laceration 32 (FIG. 7F).

The foregoing is offered primarily for purposes of illustration. It will be readily apparent to those of skill in the art that the components of needle, the steps of the method and the parameters of the invention described herein may be further modified and substituted in various ways without departing from the spirit and scope of the invention.

What is claimed is:

1. A surgical needle comprising an elongate shaft having proximal and distal ends, said distal end having an eye which can be opened and closed, said eye forming a nonhollow abutment along an edge of said eye, and means for opening and closing said eye, said opening and closing means having proximal and distal ends, said distal end containing a protuberance which abuts said abutment upon closure of said eye to present a smooth, unbroken profile along the shaft when said eye is closed.

2. The surgical needle of claim 1, wherein said means for opening and closing said eye comprises a blade.

3. The surgical needle of claim 2, wherein said elongate shaft further comprises a longitudinal gutter which at least partially contains said blade.

4. The surgical needle of claim 3, wherein the proximal end of said blade is affixable immovably to said elongate shaft by a knob protruding perpendicularly from said blade, said knob being movable along the axis of said blade such that movement of said knob toward said distal end of said elongate shaft will close said eye, and movement of said knob away from the distal end of said elongate shaft will open said eye.

5. A suturing device comprising an elongate shaft having proximal and distal ends, said distal end having an eye which can be opened and closed, said eye forming a first protuberance which forms a hook-like projection into said eye, and means for opening and closing said eye, said opening and closing means having proximal end and distal ends, said distal end containing a second protuberance which abuts said first protuberance upon closure of said eye to present a smooth, unbroken profile along the shaft when said eye is closed; and     a handle secured to said proximal end of said elongate shaft.

6. The suturing device of claim 5, wherein said means for opening and closing said eye comprises a blade.

7. The suturing device of claim 6, wherein said elongate shaft further comprises a longitudinal gutter which at least partially contains said blade.

8. The suturing device of claim 7, wherein the proximal end of said blade is affixable immovably to said elongate shaft by a knob protruding perpendicularly from said blade, said knob being movable along the axis of said elongate shaft and being a means to control the position of said blade, and wherein said elongate shaft having a maximum cross sectional dimensions of about 1.5 mm, a length of about 150 mm, and wherein said eye is located about 8 mm from said distal end of said elongate shaft.

9. The suturing device of claim 5, wherein said means for opening and closing said eye further comprises a control mechanism located at said proximal end of said elongate shaft.

10. The suturing device of claim 5, wherein said eye has a hook-like shape when open.

11. The suturing device of claim 5, wherein said elongate shaft is straight.

12. The suturing device of claim 5, wherein said elongate shaft is curved.

13. The suturing device of claim 5, wherein the cross sectional area of said elongate shaft is increased in the area surrounding said eye.

14. A surgical needle comprising:
   an elongate shaft having proximal and distal ends, said distal end forming an eye which can be opened and closed, said eye forming an abutment at one edge of said eye;
   means along said shaft for opening and closing said eye, said opening and closing means having proximal and distal ends, said distal end forming a protuberance which abuts said abutment upon closure of said eye to present a smooth, unbroken profile along the shaft when said eye is closed; and
   positioning means attaching said opening and closing means to said elongate shaft means for selectively immovably securing said opening and closing means to said elongate shaft.

15. A method of suturing a laceration in a meniscus with a needle having a closable eye comprising:
   a. from within the knee joint, passing said needle with said eye in the closed position through a selected location of said meniscus and said laceration so that said eye of said needle is exterior to the knee joint;
   b. opening said eye, placing a first end of a suture in said eye, and closing said eye;
   c. withdrawing said needle from said meniscus so that said eye is in the knee joint, said first end of a suture traverses said meniscus, and a second end of a suture remains exterior to the knee joint;
   d. passing said needle through said meniscus and said laceration in a location other than said selected location so that said eye is exterior to the knee joint;
   e. opening said eye, removing said first end of a suture from the eye, closing said eye, and withdrawing said needle so that said first end of a suture remains in place,
   f. securing said first and second ends of the suture; and
   g. repeating steps a-f until the laceration is repaired.

16. A method of claim 15, wherein said first end of a suture and said second end of a suture are opposite ends of a single suture.

17. A method of claim 15, wherein a suture is placed on the superior surface of the meniscus.

18. A method of claim 15, wherein a suture is placed on the inferior surface of the meniscus.

19. A method of suturing a laceration in a meniscus with a needle having a closable eye comprising:
   a. from outside the knee joint, placing a first end of a suture in said eye and closing said eye;
   b. passing said needle through a selected location of said meniscus and said laceration so that said eye is within said knee joint and a second end of a suture remains outside said knee joint;
   c. opening said eye, removing said first end of a suture from said eye, and closing said eye;
   d. withdrawing said needle so that said first end of a suture remains within said knee joint;
   e. passing said needle through a location of said meniscus and said laceration other than said selected location so that said eye is within said knee joint;
   f. opening said eye, placing said first end of a suture in said eye, and closing said eye;
   g. completely withdrawing said needle from within said knee joint;
   h. opening said eye and removing said first end of a suture from the eye;
   i. securing said first and second ends of a suture; and
   j. repeating steps a-i until the laceration is repaired.

20. A method of claim 19, wherein said first end of a suture and said second end of a suture are opposite ends of a single suture.

21. A method of claim 19, wherein a suture is placed on the superior surface of the meniscus.

22. A method of claim 19, wherein a suture is placed on the inferior surface of the meniscus.

* * * * *